United States Patent [19]

Hazen

[11] Patent Number: 4,966,728

[45] Date of Patent: Oct. 30, 1990

[54] ADJUVANTS FOR USE WITH POSTEMERGENT HERBICIDES

[75] Inventor: James L. Hazen, Apex, N.C.

[73] Assignee: BASF Corporation, Wyandotte, Mich.

[21] Appl. No.: 237,609

[22] Filed: Aug. 26, 1988

[51] Int. Cl.$^5$ .......................... B01J 17/34; B01J 17/44
[52] U.S. Cl. ................................ 252/354; 71/DIG. 1; 71/106; 71/123; 71/127; 252/351; 252/353; 252/356
[58] Field of Search .................. 71/DIG. 1, 123, 106, 71/127; 252/356, 351, 353, 354

[56] References Cited

U.S. PATENT DOCUMENTS

| | | | |
|---|---|---|---|
| 3,990,884 | 11/1976 | Barker | 71/DIG. 1 |
| 3,997,322 | 12/1976 | Ratledge | 71/DIG. 1 |
| 4,174,960 | 11/1979 | Hendriksen | 71/DIG. 1 |
| 4,624,696 | 11/1986 | Keil et al. | 71/94 |
| 4,642,338 | 2/1987 | Rogers et al. | 534/558 |
| 4,659,367 | 4/1987 | Keil et al. | 71/90 |
| 4,666,510 | 5/1987 | Watson et al. | 71/105 |
| 4,834,908 | 5/1989 | Hazen et al. | 252/356 |
| 4,840,660 | 6/1989 | Kowite et al. | 71/DIG. 1 |

Primary Examiner—Richard L. Raymond
Assistant Examiner—Raymond Covington
Attorney, Agent, or Firm—Bruce E. Harang

[57] ABSTRACT

Herbicide adjuvants are disclosed with enhance the effectiveness of a broad spectrum of postemergent herbicides. These adjuvants preferably contain a low foaming nonionic surfactant, an anionic surfactant, a lower alkanol ester of a fatty acid, and a hydrocarbon oil component.

10 Claims, No Drawings

ADJUVANTS FOR USE WITH POSTEMERGENT HERBICIDES

BACKGROUND OF THE INVENTION

1. Field of the Invention

The subject invention relates to adjuvants for postemergent herbicides, which fall into the category of crop oil concentrates. More particularly, the subject invention relates to improved crop oil concentrates which enhance the efficacy of herbicides, allowing greater or equal weed control while using less active ingredient.

2. Description of the Related Art

It is well established that a variety of adjuvants play important roles in the application of herbicides. These adjuvants are a diverse group of components with equally diverse functions which may often be determined from their generic names, i.e. "spreaders," "stickers," "solubilizers," "emulsifiers," "flow control agents," "drift control agents," and so on. Among the many useful herbicide adjuvants are the so-called "crop oil concentrates."

Crop oil concentrates are often recommended by herbicide manufacturers and formulators for inclusion in tank mixes to increase the efficacy of postemergent herbicide formulations. Crop oil concentrates are available from a variety of sources, and generally consist of from 75-95 percent by weight of a hydrocarbon oil or solvent with the balance being a surfactant, although in certain cases the surfactant may comprise a majority of the composition, or even all of the composition.

The hydrocarbons which form a major part of the crop oil concentrate may be derived from mineral (petroleum) or vegetable sources. When derived from mineral sources, the hydrocarbon component may be predominately paraffinic, or may be aromatic, particularly alkylated aromatic.

Although the use of selected crop oil concentrates may enhance herbicidal efficacy, it is well known that many of the proprietary concentrates available are not as effective as others. Some may even impact negatively upon herbicidal efficacy. Additionally, there is a great deal of inconsistency with regard to the make up of available crop oil concentrates. Finally, to further complicate the situation, manufacturers frequently change the formulations without notifying the consumer, resulting in a great deal of uncertainty with regard to their performance.

In recent years, the situation with respect to crop oil concentrates has achieved such a level of notoriety that some agriculturists refer to them as "snake oils." Thus there is a need in the agricultural sector, for a crop oil concentrate with a well defined make-up which is capable of enhancing the efficacy of a broad spectrum of herbicides, and which gives reproducible results.

SUMMARY OF THE INVENTION

It has now been surprisingly discovered that certain crop oil concentrates enhance the activity of a spectrum of herbicides over and above the efficacy obtained with other, commercial adjuvants. These crop oil concentrates are especially useful with cyclohexenone type herbicides, increasing their overall effectiveness by a factor of from 2 to 3.

DESCRIPTION OF THE PREFERRED EMBODIMENTS

The crop oil concentrates of the subject invention comprise a mixture of (a) a first active component which is a low foaming nonionic surfactant; (b) a second active component which is an anionic surfactant derived from esterification of a polyoxyalkylene nonionic surfactant with a dihydric or trihydric inorganic acid or by carboxylation with an organic acid derivative; and (c) optionally and preferably a third active component which is a lower alkanol ester of a long chain fatty acid, or, when the low foaming nonionic surfactant is a block or heteric surfactant containing oxyethylene and higher oxyalkylene residues, a polyoxyethylated aliphatic alcohol or mixtures of polyoxyethylated aliphatic alcohol and lower alkanol ester. As a fourth component (d), a hydrocarbon "oil" is preferably added.

The low foaming surfactants (a) are polyoxyalkylene nonionic surfactants initiated with long chain aliphatic alcohols which have little tendency to foam as measured, for example, by the Ross-Miles test. Preferably, the low foaming surfactant should have a dynamic foam height measured at 0.1 percent concentration and 50° C, of less than about 10 cm, more preferably less than 6 cm, and most preferably about 3 cm or less. The low foaming surfactants typically have hydrophile/lipophile (HLB) values of less than 12, preferably less than 8 and most preferably less than 6.

The low foaming surfactants (a) of the subject invention comprise two related types of surfactants or their mixtures. Both types of low foamers are initiated with long chain fatty alcohols having chain lengths of from 6 to 22, preferably from 10 to 18, and particularly from 13 to 15 carbons in the aliphatic hydrocarbon portion of the molecule.

One type of low foamer (a) is prepared by oxyethylating the previously described aliphatic alcohols with from 2-6 moles of ethylene oxide, preferably 3-5 moles. The second type of low foamer is prepared by oxyalkylating the aliphatic alcohol initiator with both ethylene oxide and a higher alkylene oxide, preferably propylene oxide, butylene oxide, or mixtures thereof. The oxyalkylation by the various alklene oxides may take place substantially sequentially or may take place concurrently, the product having the low foaming properties previously described.

In this second type of low foaming surfactant, from 2 to about 20 moles of ethylene oxide and from 1 to about 15 moles of higher alkylene oxide are utilized. Preferably, the oxyalkylation is sequential and involves the addition of preferably from 2 to about 12, more preferably from 2 to about 10 moles of ethylene oxide followed by the addition of from 1 to about 15, preferably from 1 to about 10 moles of higher alkylene oxide. When butylene oxide is the higher alkylene oxide, generally less higher alkylene oxide need be used than when propylene oxide is the higher alkylene oxide. From 1 to about 4 moles of butylene oxide is preferred.

When both alkylene oxides are added concurrently to form a heteric low foaming surfactant, from 2 to about 18 moles, preferably 4 to about 8 moles of ethylene oxide are used with from 2 to about 10, preferably 3 to about 7 moles of higher alkylene oxide.

The anionic surfactants (b) which are useful in the practice of the subject invention are preferably the partial sulfate and phosphate ester of polyoxyalkylene ethers. These partial esters are prepared by methods well known to those skilled in the art, for example by reacting one of the well known and commercially available monohydric polyoxyalkylene ethers with sulfuric acid or phosphoric acid or their chemical equivalents. The sulfate esters so obtained consist predominately of the half ester (monoester) while the phosphate esters generally contain both mono- and diesters. Also useful, are the carboxylate surfactants.

The methods of preparation of such surfactants are well known to those skilled in the art. The sulfate esters may be prepared, for example, by reacting a suitable monofunctional polyoxyalkylene ether with sulfuric acid or its chemical equivalent, preferably sulfamic acid or sulfur trioxide. The phosphate esters may be prepared similarly by reaction of the monofunctional polyoxyalkylene ether with phosphoric acid, diphosphorus pentoxide, polyphosphoric acid, or phosphorus oxytrichloride. In a similar manner, difunctional polyoxyalkylene ethers may be reacted with the phosphate ester producing reagent to form a surfactant containing an internal polyoxyalkylene component terminated with phosphate ester groups. Methods of preparation are described in the treatise *Nonionic Surfactants*, Martin Schick, Ed., Marcel Dekker, New York, ©1967, in Chapter 11, pp 372–394.

The nonionic, monofunctional and difunctional polyoxyalkylene ethers used to prepare the sulfate and phosphate esters are also well known to those skilled in the art, and are available commercially from many sources. Preferred nonionic polyoxyalkylene ethers have molecular weights of from about 400 to about 3000 Daltons, more preferably from about 600 to about 1200 Daltons, and particularly about 800 Daltons.

The preferred polyethers are prepared by oxyalkylating a monofunctional or difunctional initiator by known methods. Preferred initiators are the alkylphenols such as octyl- and nonylphenol, and the aliphatic alcohols, particularly the latter. The preferred aliphatic alcohols have from 6 to 30, more preferably from 10 to 20, and in particular, from 12 to 16 carbon atoms in the aliphatic residue.

The alkylene oxides which may be used to prepare the nonionic monofunctional polyoxyalkylene intermediates include ethylene oxide, propylene oxide, and butylene oxide. Tetrahydrofuran may also be useful. Preferred alkylene oxides are ethylene oxide and propylene oxide. When both these oxides are utilized, they may be added simultaneously, in sequence, or in combinations of these modes of addition, to prepare block, heteric, and block-heteric surfactants. Ethylene oxide may also be used alone to form homopolymeric polyoxyethylene polyethers.

The carboxylate surfactants are derived from oxyethylated aliphatic alcohols by reaction with chloroacetic acid in the presence of base. The preparation is described in the Schick treatise, supra, at pages 388–89. Preferably, the aliphatic alcohol contains from 6 to 30, more preferably from 10 to 20 carbon atoms, and particularly from 12 to 16 carbon atoms, and is oxyethylated with from 2 to 10, preferably from 3 to 8 moles of ethylene oxide. Preferred is the carboxylate formed from the reaction of chloroacetic acid and the four mole oxyethylate of lauryl alcohol. Reference in the specification and the claims to "carboxylates" of monohydroxyl functional polyoxyalkylene ethers is to this type of surfactant.

The lower alkanol ester of the long chain carboxylic acid (c) may be considered as derived from a lower alkanol having from 1 to 4 carbon atoms, such as methyl alcohol, ethyl alcohol, propyl alcohol, or butyl alcohol, and a long chain carboxylic acid. The methyl and ethyl esters are preferred. Most particularly, the methyl esters are utilized. The long chain carboxylic acid preferably contains from 6–22 carbon atoms, more preferably from 14–18 carbon atoms. Most preferred are those carboxylic acids obtainable from natural sources such as fats and oils, for example lauric, myristic, stearic, linoleic, linolenic, palmitic, and oleic acids. Mixtures of these acids are also useful. Preferred are oleic and palmitic acids and their mixtures. Thus the most preferred alkanol esters are methyl oleate, methyl palmitate, and mixtures of these esters. In the remainder of the specification, such compounds will be referred to as lower alkanol esters.

When the low foaming nonionic surfactant (a) is not a polyoxyethylated aliphatic alcohol, then all or part of the lower alkanol ester (c) may be replaced with a low to moderate foaming type of surfactant. Examples are the greater than 3 mole, preferably 4–6 mole oxyethylated alcohols. Such alcohols should contain from 6 to about 22 carbon atoms and may be aliphatic, cycloaliphatic, aromatic or alkylaromatic in nature. Examples of preferred replacement surfactants are the 4 mole oxyethylates of long chain aliphatic alcohols such as lauryl alcohol.

Component (d) may be derived principally from vegetable or petroleum sources. Preferred are the aromatic solvents, particularly those containing alkylated aromatics such as the benzenes and naphthalenes. Component (d) may also be a paraffinic or aromatic "oil" or solvent derived from mineral sources. Such solvents are readily available from a number of sources, for example, the Shellsolve ® solvents available from the Shell Oil Co., Houston, Texas, and the Aromatic ® 150 and 200 solvents available from the Exxon Corporation. Suitable paraffinic hydrocarbons are preferably solvent refined petroleum oil fractions composed of naphthenic as well as paraffinic hydrocarbons with less than about 25 weight percent of aromatics. Such hydrocarbon "oils" generally have high flashpoints, i.e. above 200° F., preferably above 300° F. Mixtures of paraffinic and aromatic hydrocarbons may also be used.

The hydrocarbon component (d) may also contain up to about 30 percent by weight, preferrably from 10–30 percent by weight of a solvent soluble alcohol, for example n-hexanol or isooctanol, to maintain or enhance the physical properties of the blend. Other solvent soluble alcohols which are suitable are those which generally contain from 5 to about 18 carbon atoms, preferably from 5 to about 10 carbon atoms. The term "hydrocarbon component" as used herein should be taken as including both aliphatic and aromatic solvents as well as their mixtures, including also the solvent soluble alcohol component described immediately above. The hydrocarbon component is believed to exert a minor biochemical effect in concert with that of the remaining ingredients, and hence may be considered an active ingredient.

When utilized as a crop oil concentrate without the hydrocarbon component, the composition generally contains, in percent by weight relative to the total weight of the concentrate, from 20 to 90 percent low foaming surfactant (a), 4 to 40 percent anionic surfactant (b), and 0 to 30 percent lower alkanol ester (c). Preferably, the composition contains 30 to 80 percent low foaming surfactant, 4 to 20 percent anionic surfactant, and 2 to 16 percent lower alkanol ester. Most preferably it contains 70 to 80 percent low foaming surfactant, 5 to 10 percent anionic surfactant, and 4 to 12 percent lower alkanol ester.

The preferred hydrocarbon component-containing crop oil concentrates generally contain, in percent by weight relative to the total weight of the crop oil concentrate, from about 10 to about 60 percent of low foaming surfactant, from about 2 to about 20 percent anionic surfactant, from 0 to about 20 percent lower alkanol ester, and from 70 to about 30 percent hydrocarbon component. More preferably, the crop oil concentrate contains from 25 to 45 percent low foaming surfactant, 2 to about 10 percent anionic surfactant, 2 to 8 percent lower alkanol ester, and 60 to 40 percent hydrocarbon component. Most preferably, the crop oil concentrate contains from about 35 to about 40 percent low foaming surfactant, from about 5 to about 10 percent anionic surfactant, from about 4 to 7 percent lower alkanol ester, and about 50 percent hydrocarbon component. The hydrocarbon component may optionally contain up to about 30 percent, preferably from 10 to about 20 percent, and most preferably about 18 percent of a solvent soluble alcohol.

The crop oil concentrates of the subject invention may be utilized in tank mixes for many postemergent herbicide formulations, generally in amounts of from about 0.5 to about 8 l/HA, preferably from about 2 to about 5 l/HA. Many manufacturers recommend the use of crop oil concentrates for particular applications or, in some cases, for all applications of their herbicides. In other cases, the concentrates may be used as experience dictates. The subject invention crop oil concentrates may be used in conjunction with a nitrogen source such as urea, ammonium sulfate, ammonium nitrate, ammonium phosphate and the like.

The crop oil concentrates of the subject invention have been found effective with herbicides of diverse chemical structure, for example with the cyclohexenone herbicides, the benzothiadiazinonedioxide herbicides, the diphenylether herbicides, the quinolinecarboxylic acids and the aryloxyphenoxy herbicides including analogues containing heterocycles such as the quinoxalinyloxyphenoxy herbicides. The crop oil concentrates are especially effective with the cyclohexenone-type herbicides.

The cyclohexenone herbicides with which the subject invention crop oil concentrates may be used are well known. Examples of their preparation and use may be found in U.S. Pat. Nos. 3,950,420; 4,011,256, 4,249,937, and 4,666,510. Specific mention may be made of certain of the more common cyclohexenones, including alloxydim, sethoxydim, cycloxydim, clethodim, and cloproxydim.

The diphenyl ether herbicides and their analogues are likewise well known. These herbicides are described, for example, in chapter 14 of Herbicides, P. C. Kearney et. al., published by Marcel Dekker, Inc., New York © 1976. Many other classes of herbicides are also described in this two volume treatise. Also well known are the dipyridilium herbicides such as paraquat, diquat, and morfamquat.

In addition to the use of the crop oil concentrates as herbicides adjuvants, they are also useful in promoting the biological activity of various other pesticides such as fungicides, mildewcides, defoliants, and insecticides and plant growth regulators.

In the examples which follow, herbicides or herbicide mixtures are tested for their efficacy against a variety of common weeds. In many cases, comparisons are made to similar tank mix compositions but containing other crop oil concentrates. The "standard" crop oil concentrate used for comparison purposes is "Booster Plus E," a product of the Agway Corporation. This product has been widely used in herbicide applications and appears to have consistent formulation and product quality. In the examples, this "standard" crop oil concentrate is labeled "OC". In all the tables showing efficacy of the crop oil concentrate/herbicide mixtures against various species of weeds, the numerical values in the tables represent the percentage of weed control, or percent kill of the various species.

Examples 1–6

Postemergent herbicide adjuvants (crop oil concentrates) were prepared in accordance to the formulations presented in Table I. The ingredients were mixed in the order indicated, all parts being parts by weight.

TABLE I

| Ingredient[1] | 1 | 2 | 2a | 3 | 4 | 5 | 6 |
|---|---|---|---|---|---|---|---|
| Lutensol ® AO 3 | 75 | | | | | | |
| Plurafac ® LF 700 | | 75 | 75 | 75 | 37.5 | 37.5 | 37.5 |
| Macol ® LA-4 | | | | | | 5.0 | |
| Klearfac ® AA 270 anionic surfactant | | | 15 | 15 | 7.5 | 7.5 | 7.5 |
| Atphos ® 3220 | 15 | 15 | | | | | |
| Mixed alkanol esters | 10 | 10 | 10 | 10 | 5.0 | | 5.0 |
| Aromatic ® 150 | | | | | 50.0 | 50.0 | 40.0 |
| Isooctanol | | | | | | | 10.0 |
| Total (percent) | 100 | 100 | 100 | 100 | 100 | 100 | 100 |

[1]Lutensol ® AO 3 is a 3 mole oxyethylated $C_{13}$-$C_{15}$ oxo alcohol available from BASF Akiengesellschaft, D-6700 Ludwigshafen, FRD; Plurafac ® LF 700 is a low foaming, fatty alcohol initiated REP block polyoxyalkylene surfactant having a nominal molecular weight of approximately 900 Daltons available from BASF Corporation, Parsippany, New Jersey; Macol ® LA-4 is a 4 mole oxyethylated lauryl alcohol available from Mazer Chemical Co.; the mixed alkanol esters are C-65 ® methylester, a product available from the Stepan Chemical Co., an approximately 1:1 blend of methyloleate and methylpalmitate derived from natural sources;
Atphos ® 3220 is a experimental phosphate ester surfactant available from ICI Americas Corp.
Klearfac ® AA270 is a phosphate ester surfactant derived from a nonionic polyether having a molecular weight of about 800 Daltons, available from BASF Corp., Parsippany, N.J.;
Aromatic ® 150 solvent is a mixed aromatic solvent available from the Exxon Chemical Corporation.

In comparing the efficacy of the subject invention crop oil concentrates with alternative crop oil concentrates, the respective concentrates were added at levels of generally from 1 to 5 l/HA to tank mixes of the herbicides and agitated to prepare a uniform mixture. Cyclohexenone herbicides A, B, C, and D are experimental cyclohexenones of the type disclosed in U.S. Pat. Nos. 4,249,937, 4,011,256, and 3,950,420.

Standard abbreviations for the various weed species found in the text which follows may be found below:

| ABUTH | Abutilon theophrusti | velvet leaf |
|---|---|---|
| AVEFA | Avena fatua | wild oats |
| AVESA | Avena sativa | oats (volunteer) |
| BRAPP | Brachiaria platyphylla | broadleaf signal grass |
| BROSE | Bromus secalinus | cheatgrass |
| CHEAL | Chenopodium album | common lambsquarter |
| CYNDA | Cynodon dactylon | bermudagrass |
| DAOTE | Daubentonia texana | coffee weed |
| DATST | Datura stramonium | jimsonweed |
| DIGSA | Digitoria sanguinalis | large crabgrass |
| ECHCG | Echinochloa crus-galli | barnyardgrass |
| FESAR | Festuca arundinacea | tall fescue |
| HORVX | Hordeum vulgare | barley (volunteer) |
| IPOLA | Ipomoea lacunosa | pitted morning glory |
| IPOSS | Ipomoea spp. | morningglory species |
| LEFFI | Leptochloa filiformis | red sprangletop |
| LOLMU | Lolium multiflorum | annual ryegrass |
| PANTE | Panicum texanum | Texas panicum |
| POAAN | Poa annua | annual bluegrass |
| POAPR | Poa pratensus | Kentucky bluegrass |
| SETFA | Setaria faberii | giant fox tail |
| SETLU | Setaria lutescens | yellow foxtail |
| SETVI | Setaria viridis | green foxtail |
| SORHA | Sorghum halepense | Johnson grass |
| TRZAX | Triticum aestivum | wheat (volunteer) |
| TRFSS | Trifolium spp. | Clover species |
| XANPE | Xanthium pennsylvanicum | cocklebur |
| ZEAMD | Zea maydis | corn (dent) |
| ZEAMX | Zea mays | corn (volunteer) |

In Table II is shown the greater effectiveness of the crop oil concentrate of Example 3 when used with a defoliation agent, thidiazuron, in preventing regrowth of cotton. The comparative adjuvant is surfactant "WK," a Product of E. I. duPont de Nemours & Company.

TABLE II

| Cotton Defoliation and Regrowth at 150 g active/HA | | |
|---|---|---|
| Adjuvant[1] | Defoliation, %[2] | Regrowth[3] |
| Crop oil concentrate of Example 1 | 100 | 0.2 |
| Surfactant WK | 100 | 2.4 |

[1] @ 0.25 l/HA
[2] Defoliation evaluated 6 DAT (days after treatment)
[3] Regrowth on 0–10 scale 24 DAT; 0 = no regrowth; 10 = 100% regrowth.

In Table III is summarized the increased effectiveness of cycloxydim in combatting volunteer oats, barley, and wheat in peas (var. "Progress 9").

TABLE III

| Weed Control in Peas by Cycloxydim at 100 g/HA | | | | |
|---|---|---|---|---|
| Crop Oil Concentrate[1] | Weed Species: | | | |
| | HORVX | LOLMU | TRZAX | OVERALL |
| OC | 40 | 99 | 27 | 55 |
| Example 3 | 76 | 99 | 54 | 77 |

TABLE III-continued

| Weed Control in Peas by Cycloxydim at 100 g/HA | | | | |
|---|---|---|---|---|
| Crop Oil Concentrate[1] | Weed Species: | | | |
| | HORVX | LOLMU | TRZAX | OVERALL |
| Example 6 | 89 | 99 | 81 | 90 |

[1] Oil concentrates at 2 l/HA

In Table IV, the greater effectiveness of the subject invention over the standard concentrate is demonstrated against various grass species in alfalfa.

TABLE IV

| Weed Control by Sethoxydim @ 150 g/HA Using Various Adjuvants | | | | | |
|---|---|---|---|---|---|
| Adjuvants[1] | Weed Species | | | | |
| | HORVX | SETLU | DIGSA | ZEAMX | TRZAX |
| OC | 80 | 99 | 88 | 75 | 70 |
| Example 3 | 84 | 98 | 94 | 83 | 76 |
| OC + 5 Kg/HA Ammonium sulfate | 88 | 98 | 95 | 87 | 80 |
| Example 3 + 5 Kg/HA Ammonium sulfate | 92 | 99 | 98 | 96 | 90 |

[1] Crop oil concentrates at 2 l/HA

In Table V summarizes the effectiveness of a crop oil concentrate of the subject invention as compared to the standard concentrate when added to sethoxydim formulations for grass control in peas.

TABLE V

| Weed Control in Peas with Sethoxydim at 150 g/HA | | | | |
|---|---|---|---|---|
| Adjuvant | Weed Species: | | | |
| | HORVX | LOLMU | TRZAX | OVERALL |
| OC | 97 | 91 | 73 | 79 |
| Example 3 | 100 | 100 | 94 | 95 |

In Table VI, weed control in soybeans was assessed 29 DAT using sethoxydim at 150 g/HA and various crop oil concentrates at 2 l/HA.

TABLE VI

| Weed Control in Soybeans Using Sethoxydim @ 150 g/HA with Various Adjuvants | | | | |
|---|---|---|---|---|
| Adjuvant[1] | Weed Species: | | | |
| | LOLMU | TRZAX | BROSE | OVERALL |
| OC | 80 | 47 | 23 | 56 |
| Example 2 | 83 | 70 | 25 | 70 |
| Example 2a | 85 | 77 | 37 | 77 |
| Example 3 | 83 | 63 | 33 | 62 |

[1] All adjuvants at 2 l/HA

Table VII indicates the greater effectiveness of the crop oil concentrates of the subject invention in controlling volunteer corn using sethoxydim at a rate of 100 g/HA and various adjuvants at c.a. 2 l/HA.

TABLE VII

| Volunteer Corn Control Using 100 g/HA Sethoxydim and Various Adjuvants | | |
|---|---|---|
| Adjuvant | ZEAMX (30 DAT) | ZEAMX (40 DAT) |
| OC | 40 | 46 |
| Example 1 | 75 | 79 |
| Example 2a | 73 | 65 |
| Example 2 | 82 | 89 |
| Example 3 | 85 | 86 |

In Table VIII, Sethoxydim control of grass species in peas is assessed with various adjuvants. Sethoxydim was applied as a tank mix at the rate of 100 g/HA with adjuvant at 2 l/HA.

TABLE VIII

| | Sethoxydim Control of Grass Species in Peas at 42 DAT | | | |
|---|---|---|---|---|
| | Weed Species: | | | |
| Adjuvant | DIGSA | LEFFI | ECHCG | OVERALL |
| OC | 98 | 43 | 98 | 74 |
| Example 3 | 98 | 51 | 98 | 79 |
| Example 4 | 99 | 93 | 99 | 96 |

In Table IX is demonstrated the greater control of bermudagrass and johnsongrass by cycloxydim at 200 g/Ha in the presence of various adjuvants at 1.0 weight percent in the tank mix.

TABLE IX

| Control of Grasses by cycloxydim in the Presence of Various Adjuvants at 13 DAT | | |
|---|---|---|
| | Grass Species: | |
| Adjuvant | CYNDA | SORHA |
| OC | 29 | 57 |
| Example 3 | 42 | 82 |
| Example 4 | 47 | 82 |
| Example 5 | 47 | 85 |

Table X demonstrates the increased herbicidal activity of bentazon, [3-(1-methylethyl-1H-2,1,3-benzothiadiazin-4(3H)-one-2,2-dioxide] in broadleaf weed control in soybeans during greenhouse trials. Bentazon was used at the rate of 480 g/HA.

TABLE X

| Broadleaf Weed Control Enhancement by Various Adjuvants | | | | |
|---|---|---|---|---|
| | Weed Species: | | | |
| Adjuvant[1] | TRFSS | ABUTH | DATST | IPOSS |
| OC | 0 | 75 | 98 | 52 |
| Example 3 | 7 | 80 | 98 | 87 |

[1]Adjuvants at 2 l/HA

Table XI demonstrates the greater effectiveness of the subject invention crop oil concentrate as compared to a crop oil concentrate Assist ® which is widely used in Canada. Control of three weed species 41–43 days after treatment averaged from 4–5 locations is presented. The herbicide is Sethoxydim used at 150 g/HA.

TABLE XI

| Grass Weed Control in the Presence of Adjuvants | | | |
|---|---|---|---|
| | Weed Species: | | |
| Adjuvant | TRZAX | HORVX | AVEFA |
| Assist ® | 79 | 84 | 90 |
| Example 6 | 80 | 97 | 94 |

Table XII demonstrates the increase effectiveness of the subject invention crop oil concentrates on volunteer barley and wheat 42 DAT.

TABLE XII

| Adjuvant Effectiveness in Combating Volunteer Weeds | | |
|---|---|---|
| | Weed Species: | |
| Adjuvant | HORVX | TRZAX |
| OC | 78 | 77 |
| Example 6 | 98 | 98 |

TABLE XIII

| Grass Control With Quinolac at 280 g/HA[1] | | |
|---|---|---|
| Adjuvant | Adjuvant Rate, l/HA | % Grass Control[2] |
| none | — | 40 |

TABLE XIII-continued

| Grass Control With Quinolac at 280 g/HA[1] | | |
|---|---|---|
| Adjuvant | Adjuvant Rate, l/HA | % Grass Control[2] |
| OC | 2.3 | 55 |
| DASH ™[3] | 2.3 | 48 |
| Example 3 | 2.3 | 66 |

[1]Greenhouse test using a track sprayer with herbicide tank mix delivery at 20 gal/A. Evaluations 14 DAT.
[2]Average of 6 grass species: BRAPP, SETVI, ECHCG, DIGSA, AVEFA, ZEAMX.
[3]A crop oil concentrate of the BASF Corporation, Parsippany, NJ.

TABLE XIV

| Grass Control in Rice with Quinolac at 60 g/HA | | | |
|---|---|---|---|
| Adjuvant | @ Rate | Rice Damage | ECHCG Control |
| Atplus ® 411 | @ 1 l/HA | 0 | 68 |
| | @ 4 l/HA | 10 | 85 |
| Citowett | @ 1 l/HA | 10 | 68 |
| | @ 4 l/HA | 20 | 72 |
| Example 3 | @ 1 l/HA | 0 | 85 |
| | @ 4 l/HA | 0 | 96 |

[1]Atplus ® 411 is a trademark of ICI Americas, Inc.
[2]Citowett ® is a trademark of BASF A. G.

Tables XIII and XIV demonstrate the greater effectiveness of the subject invention crop oil concentrates with quinolac. In rice, in particular, the crop oil concentrate at 4 l/HA with no damage to the crop. In contrast, other commercial crop oil concentrates were both less effective against barnyard grass but also exhibited crop damage.

The embodiments of the invention in which an exclusive privilege or property is claimed are defined as follows:

1. A postemergent herbicide adjuvant suitable for use in tank mixes, comprising, in percent by weight,
    (a) from about 20 to about 90 percent of a low foaming nonionic surfactant selected from the group consisting of
        (i) alkylpolyoxyethylene polyethers wherein the alkyl group contains from 6 to about 22 carbon atoms and the polyoxyethylene moiety is derived from 3 to about 6 moles of ethylene oxide; and
        (ii) alkylpolyoxyalkylene polyethers wherein the alkyl group contains from 6 to about 22 carbon atoms and the polyoxyalkylene moiety is derived from ethylene oxide and a higher alkylene oxide, and wherein the polyether has an HLB of less than about 12; and
        (iii) mixtures thereof
    (b) from 4 to about 40 percent of an anionic surfactant selected from the group consisting of
        (i) the partial sulfate and phosphate esters and carboxylates of monohydroxyl-functional polyoxyalkylene ethers; and
        (ii) the partial phosphate esters of dihydroxyfunctional polyoxyalkylene ethers; and
    (c) 0 up to about 20 percent of a third component selected from the group consisting of
        (i) the lower alkanol esters of 6 to 22 carbon carboxylic acids;
        (ii) when component (a) is not present, the alkylpolyoxyethylene polyethers wherein the alkyl group contains 6 to about 22 carbon atoms and the polyoxyethylene moiety is derived from 3 to about 8 moles of ethylene oxide.

2. The adjuvant of claim 1 wherein the low foaming surfactant (a) is present in an amount of from 30 to about 80 percent, the anionic surfactant (b) is present in an amount of from 4 to about 20 percent, and component (c) is present in an amount of from 2 to about 16 percent.

3. The adjuvant of claim 1 wherein the low foaming surfactant a) is present in an amount of from 70 to about 80 percent, the anionic surfactant b) is present in an amount of from 5 to about 10 percent, and component (c) is present in an amount of from 4 to about 12 percent.

4. A postemergent herbicide adjuvant suitable for use in tank mixes, comprising, in percent by weight,
   (a) from 20 to about 80 percent of the adjuvant of claim 1; and
   (b) from 80 to about 20 percent of a hydrocarbon component containing from 100 to 70 weight percent based on the total weight of the (b) component of a hydrocarbon oil selected from the group consisting of
      (i) an aromatic hydrocarbon component;
      (ii) an aliphatic hydrocarbon component,
      (iii) mixtures thereof;
   and from 0 to about 30 weight percent of a solvent soluble alcohol component.

5. A postemergent herbicide adjuvant suitable for use in tank mixes, comprising, in percent by weight,
   (a) from 20 to about 80 percent of the adjuvant of claim 2; and
   (b) from 80 to about 20 percent of a hydrocarbon component containing from 100 to 70 weight percent based on the total weight of the (b) component of a hydrocarbon oil selected from the group consisting of
      (i) an aromatic hydrocarbon component;
      (ii) an aliphatic hydrocarbon component,
      (iii) mixtures thereof;
   and from 0 to about 30 weight percent of a solvent soluble alcohol component.

6. A postemergent herbicide adjuvant suitable for use in tank mixes, comprising, in percent by weight,
   (a) from 20 to about 80 percent of the adjuvant of claim 3; and
   (b) from 80 to about 20 percent of a hydrocarbon component containing from 100 to 70 weight percent based on the total weight of the (b) component of a hydrocarbon oil selected from the group consisting of
      (i) an aromatic hydrocarbon component;
      (ii) an aliphatic hydrocarbon component,
      (iii) mixtures thereof;
   and from 0 to about 30 weight percent of a solvent soluble alcohol component.

7. The adjuvant of claim 1 wherein said low foaming surfactant a) is an alkylpolyoxyalkylene polyether containing from 2 to about 20 oxyethylene moieties and from 1 to about 15 higher polyoxyalkylene moieties selected from the group consisting of polyoxypropylene and polyoxybutylene, and wherein said alkyl group has from 10 to about 18 carbon atoms.

8. The adjuvant of claim 3 wherein said low foaming surfactant a) is an alkylpolyoxyalkylene polyether containing from 2 to about 20 oxyethylene moieties and from 1 to about 15 higher polyoxyalkylene moieties selected from the group consisting of polyoxypropylene and polyoxybutylene, and wherein said alkyl group has from 10 to about 18 carbon atoms.

9. The adjuvant of claim 4 wherein said low foaming surfactant a) is an alkylpolyoxyalkylene polyether containing from 2 to about 20 oxyethylene moieties and from 1 to about 15 higher polyoxyalkylene moieties selected from the group consisting of polyoxypropylene and polyoxybutylene, and wherein said alkyl group has from 10 to about 18 carbon atoms.

10. The adjuvant of claim 7 wherein said low foaming surfactant (a) is an alkylpolyoxyalkylene polyether containing from 2 to about 20 oxyethylene moieties and from 1 to about 15 higher polyoxyalkylene moieties selected from the group consisting of polyoxypropylene and polyoxybutylene, and wherein said alkyl group has from 10 to about 18 carbon atoms.

* * * * *